United States Patent [19]

Haber

[11] Patent Number: 4,727,887
[45] Date of Patent: Mar. 1, 1988

[54] HYPODERMIC MANOMETER

[75] Inventor: Terry M. Haber, Lake Forest, Calif.

[73] Assignee: Habley Medical Technology Corporation, Laguna Hills, Calif.

[21] Appl. No.: 752,955

[22] Filed: Jul. 8, 1985

[51] Int. Cl.⁴ .............................................. A61B 5/00
[52] U.S. Cl. ............................. 128/748; 128/DIG. 25; 73/744
[58] Field of Search .................. 128/748, 672–675, 128/678, 684, 774, DIG. 25; 73/744, 729, 747–748; 33/511–512, 178 R

[56] References Cited

U.S. PATENT DOCUMENTS

| | | | |
|---|---|---|---|
| 2,039,337 | 5/1936 | Nolan | 128/678 |
| 3,648,687 | 3/1972 | Ramsey, III | 128/673 |
| 3,720,201 | 3/1973 | Ramsey, III | 128/748 |
| 4,023,416 | 5/1977 | Ormsby | 73/744 |
| 4,136,560 | 1/1979 | Gellos | 73/744 X |
| 4,282,881 | 8/1981 | Todd et al. | 128/675 X |
| 4,399,809 | 8/1983 | Bard et al. | 128/DIG. 25 X |
| 4,509,267 | 4/1985 | Flaten | 33/178 R X |
| 4,571,749 | 2/1986 | Fischell | 128/DIG. 25 |
| 4,574,629 | 3/1986 | Weng | 73/744 X |

Primary Examiner—William E. Kamm
Assistant Examiner—Angela D. Sykes
Attorney, Agent, or Firm—Morland C. Fischer

[57] ABSTRACT

A combination hypodermic syringe and manometer for simultaneously imparting fluid to an external device, such as a hollow occlusion cuff surrounding a patient's urethra, while at the same time providing an accurate indication of both the internal pressure within the manometer as well as the external occlusive pressure being applied to the patient's urethra by the occlusion cuff. The hypodermic manometer includes a piston assembly which is adapted for reciprocal movement through a fluid filled sleeve, whereby to force fluid from the sleeve into the occlusion cuff via a hypodermic syringe. Calibrated indicia marked on the manometer provides an indication of the internal pressure therewithin as well as the external occlusive pressure being applied to the patient's urethra.

13 Claims, 4 Drawing Figures

HYPODERMIC MANOMETER

BACKGROUND OF THE INVENTION

As will be known to those skilled in the art, in cases where the natural sphincter muscles of a patient have been excised during surgery, an artificial sphincter is often implanted in order to apply occlusive pressures to a lumen (e.g. a urethra) for holding a patient continent. Such an artificial sphincter often includes an occlusion cuff to surround and articulate the urethra and thereby achieve coaptive continence. The occlusion cuss is sometimes filled with fluid so that a corresponding inflation thereof generates occlusive pressures to be applied to the urethra. In certain cases it is desirable for the physician to controllably deliver an additional supply of fluid to the urethra, whereby to produce the minimal amount of occlusive pressure necessary to achieve coaptive continence according to the tissue requirements of the patient. For an example of the aforementioned artificial sphincter, reference may be made to the copending patent application Ser. No. 752,137, filed on July 5, 1985. However, no relatively inexpensive, easily operable device is known by which to permit a physician to deliver fluid to the occlusion cuff while at the same time ascertaining an accurate approximation of the occlusive pressures being applied to the patient's urethra.

SUMMARY OF THE INVENTION

Briefly, and in general terms, the combination hypodermic manometer which forms the present invention comprises a piston assembly which is adapted for reciprocal movement through a fluid filled sleeve. The piston assembly includes a cylindrical outer collar and a cylindrical inner core, which collar and core are coaxially arranged relative to one another. At the distal end of the core is connected a flexible, fluid filled bellows transducer. A fluid channel is formed through the piston assembly core so as to communicate with the bellows fluid. As the piston assembly is moved (i.e. downwardly) through the sleeve, the bellows is compressed and fluid from the sleeve is forced into a tube for delivery to a fluid filled occlusion cuff via a syringe. Calibrated indicia is marked upon the piston assembly to indicate the external occlusive urethral pressure, depending upon both the circumference of the urethra around which the occlusion cuff is placed and the height of the bellows fluid within the piston assembly fluid channel in response to the compression of the bellows.

DESCRIPTION OF THE PREFERRED EMBODIMENT

Figures 1, 2:
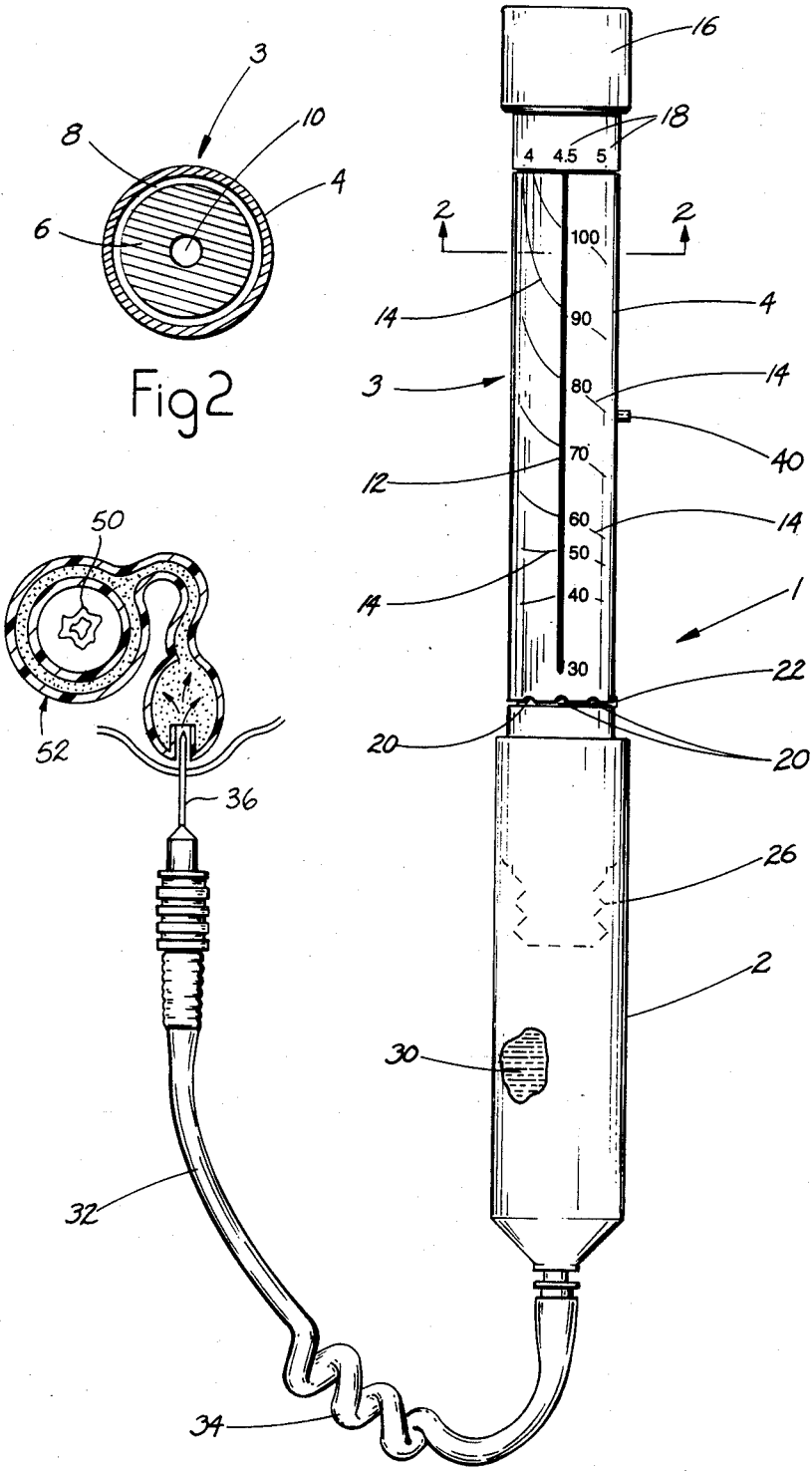
FIG. 1 is a front elevation of the hypodermic manometer which forms the present invention.
FIG. 2 is a cross section taken along lines 2—2 of FIG. 1.

The combination hypodermic manometer 1 is best described while referring concurrently to FIGS. 1–4 of the drawings. Manometer 1 includes a hollow, fluid filled sleeve or barrel 2 and a piston assembly 3 which is adapted for reciprocal movement through the sleeve 2. Piston assembly 3 comprises an outer cylindrical collar 4 and an inner cylindrical core 6. Outer collar 4 is preferably manufactured from a transparent medical grade material, such as polycarbonate or acrylic. Inner core 6 is also preferably manufactured from a transparent material, such as suitable plastic. Outer collar 4 and inner core 6 are coaxially arranged relative to one another so that a small gap 8 (best shown in FIG. 2) is formed therebetween. As will soon be explained, the outer collar 4 is adapted to be rotated relative to the inner core 6. A longitudinally extending fluid channel 10 is formed through the inner core 6.

A readout hairline 12 is printed on the outer collar 4 of piston assembly 3 so as to extend longitudinally therealong. A series of reference pressure lines 14 are printed on the inner core 6. Pressure lines 14 are arranged in a spaced relationship with one another so as to traverse hairline 12. The reference lines 14 are calibrated so as to indicate pressure in centimeters of water. More particularly, and in a manner soon to be described, the reference lines 14 are calibrated so as to convert internal pressure within the hypodermic manometer 1 into external pressure (e.g. such as the occlusive pressures being applied to a patient's urethra from a continence producing, fluid filled occlusive cuff).

Hypodermic manometer 1 also includes a piston actuator end cap 16 which is positioned adjacent the proximal end of piston assembly 3 and connected to the inner core 6 thereof. Located within cap 16 at the end of fluid channel 10 is a flexible (e.g. silicone) membrane 17 which is adapted to expand to accommodate excessive pressures within channel 10 and thereby avoid damage to the inner core 6. Printed around a bottom end surface of end cap 16 is indicia 18 corresponding to the circumference of a patient's urethra 50 around which the occlusion cuff 52 is placed. Prior to injection, the physician grasps the outer collar 4 and rotates the collar until the reference hairline 12 is aligned with the particular setting 18 at end cap 16 corresponding to the circumference of the patient's urethra 50. In this manner, the hypodermic manometer 1 may be initialized so as to convert internal manometer pressure to external pressure at the occlusion cuff 52.

Figure 3:
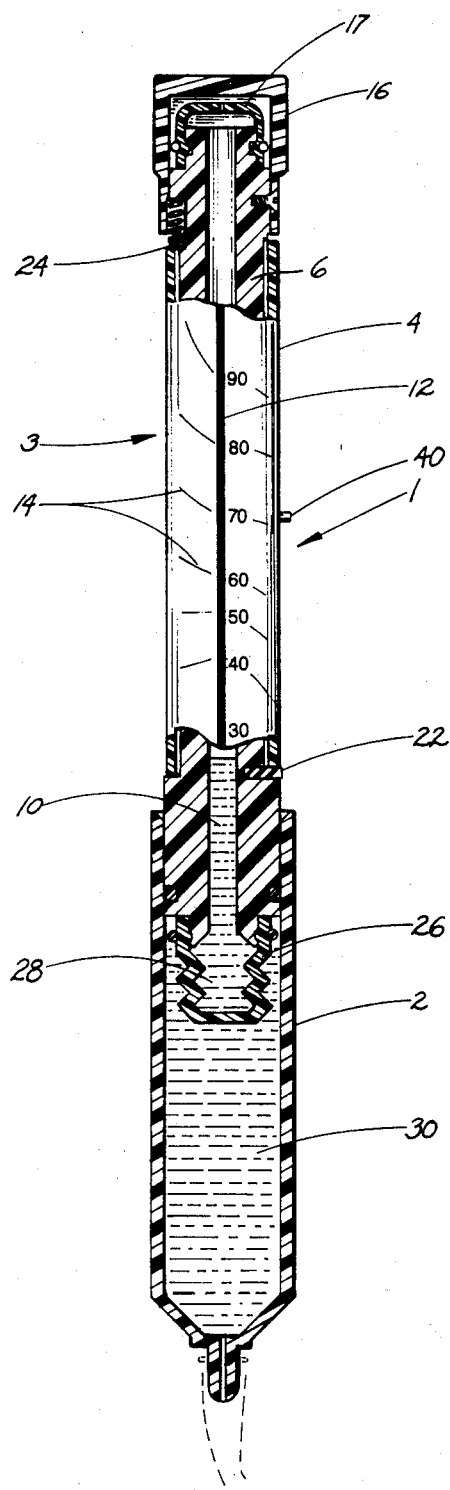
FIG. 3 is a partial cross section of the hypodermic manometer of FIG. 1 in the pre-injection state.

The bottom end surface of outer collar 4 is provided with a series of detents 20 spaced therearound. As is best shown in FIG. 3, the position of outer collar 4 is spring biased relative to the end cap 16. In order to rotate the outer collar 4, the physician lifts the outer collar against the bias of the spring (designated 24 in FIG. 3). Rotating the collar also rotates the detents 20. When the proper urethral circumferential setting is located at end cap 16, the outer collar 4 is lowered by the memory of spring 24. One of the detents 20 will be aligned to receive a stationary index pin 22, which pin is affixed to inner core 6. The receipt of indexing pin 22 by a detent 20 acts as a positive locking feature by which to prevent the inadvertent rotation of outer collar 6 during the operation of the hypodermic manometer 1 to impart fluid to the occlusion cuff.

Figure 4:
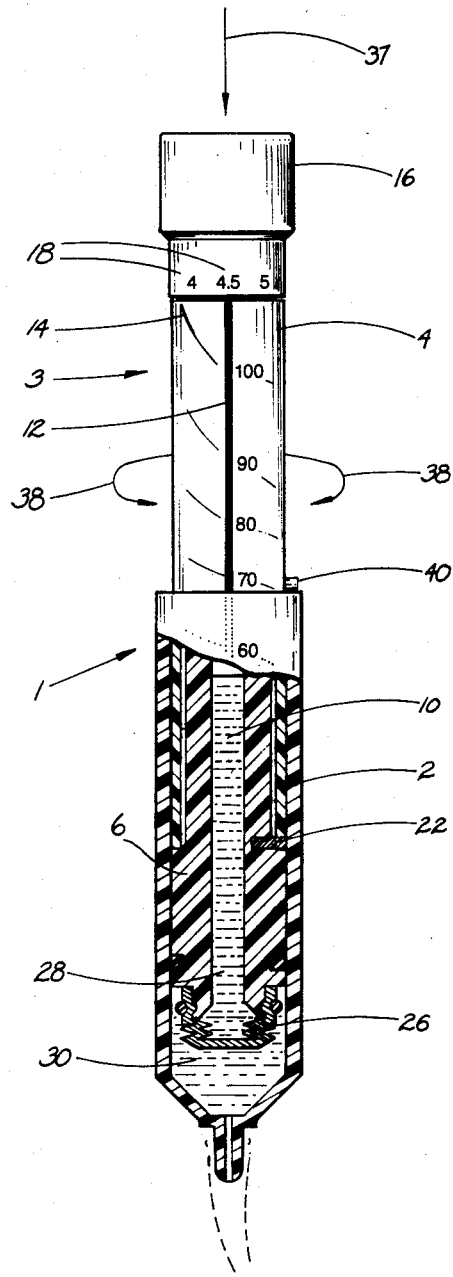
FIG. 4 is a partial cross section of the hypodermic manometer in an infused state.

Secured to the distal end of inner core 6 is a pressure transducer 26. In the preferred embodiment, the transducer assembly 26 comprises a hollow bellows which is manufactured from a flexible (e.g. silicone) material. However, it is to be understood that any other suitable pressure responsive diaphram or electromechanical pressure transducer may be substituted therefor. The bellows 26 is adapted to travel through the hollow sleeve 2 when piston assembly 3 is moved therethrough. As is best shown in FIGS. 3 and 4, the bellows 26 is filled with a fluid, such as, for example, a biocompatible dye. The hollow bellows 26 communicates with the fluid channel 10 so that the bellows fluid 28 may rise upwardly therein. The sleeve 2 is filled with a suitable isotonic fluid 30 which is to be dispensed from hypodermic manometer 1 and injected into the occlusion cuff surrounding the patient's urethra.

One end of a section of flexible tubing 32 is attached to a fluid outlet of sleeve 2. Flexible tubing 32 is manufactured from a suitable material, such as, for example, silicone and may include a force absorbing, kink-resistant, helically wound section 34. The other end of tubing 32 is interfaced with a conventional (e.g. one inch, 25 gauge) hypodermic syringe 36, by which the fluid 30 within sleeve 2 can be delivered to the occlusion cuff in the manner that will now be described while referring to FIGS. 3 and 4.

FIG. 3 shows the hypodermic manometer 1 in a pre-injection state. That is, the sleeve 2 has a full reservoir supply of fluid 30 to be delivered to an occlusion cuff; piston assembly 3 is raised to the uppermost position relative to sleeve 2; and bellows 26 is in a relaxed, non-compressed state. In operation, the physician determines the circumference of the patient's urethra around which an occlusion cuff has been placed. As has previously been indicated, the outer collar 4 is rotated until the hairline 12 of collar 4 is aligned with the appropriate circumferential setting 18 at end cap 16.

FIG. 4 shows the hypodermic manometer 1 in an infused state. That is, the physician exerts a downward force (in the direction represented by arrow 37) upon end cap 16 while, at the same time, rotating the piston assembly 3 (in either direction represented by the arrows 38). An outwardly extending limit pin 40 is associated with piston assembly 3 to limit the downward movement of piston assembly 3 through the sleeve 2 so as to prevent damage to assembly 3. Accordingly, the piston assembly 3 is moved downwardly trough the sleeve 2, and the bellows 26 is compressed so as to force the fluid 28 therein upwardly through the channel 10. Moreover, the reservoir volume of fluid in sleeve 2 is reduced, and the fluid 30 within sleeve 2 is forced outwardly therefrom and into the tubing (designated 32 in FIG. 1) for delivery to the occlusion cuff.

During the time that fluid is forced from the sleeve 2, the physician may easily and accurately ascertain the internal pressure within sleeve 2 as well as an accurate approximation of the external fluid pressure being applied to the patient's urethra by the fluid filled occlusion cuff. Such pressure may be indicated by the height of the fluid column 28 in piston assembly channel 10 relative to the reference pressure lines 14. By way of example only, the pressure indicated by the hypodermic manometer of FIG. 4 is 55 centimeters of water.

It will be apparent that while a preferred embodiment of the invention has been shown and described, various modifications and changes may be made without departing from the true spirit and scope of the invention.

Having thus set forth a preferred embodiment of the present invention, what is claimed is:

1. A hypodermic manometer comprising a fluid filled sleeve and piston assembly means for movement through said sleeve to force fluid outwardly therefrom for delivery to a hollow occlusion cuff to be implanted in engagement with the urethra of an incontinent patient for applying occlusive pressure thereto, said piston assembly means comprising a fluid channel and a fluid filled flexible bellows, said bellows and said channel communicating with one another,
   said piston assembly means further comprising pressure indicating means being movable with said piston assembly means through said sleeve to indicate the occlusive pressure being applied to the patient's urethra by said cuff, said indicating means being responsive to the height of the bellows fluid within said fluid channel when said flexible bellows is compressed during the movement of said piston assembly means through said sleeve.

2. A hypodermic manometer for delivering fluid to a utilization device, said manometer including a hollow outer sleeve containing a supply of the fluid to be delivered to the utilization device and piston assembly means located at the interior of said outer sleeve for movement therethrough to force fluid outwardly from said sleeve, said piston assembly means comprising:
   an inner core,
   an outer collar surrounding said inner core,
   resilient pressure responsive means filled with a fluid and located at one end of said piston assembly means for movement with said piston assembly means through said outer sleeve, the movement of said piston assembly means through said sleeve causing a compression of said pressure responsive means and a reduction in the volume of the fluid supply within said sleeve,
   fluid channel means extending longitudinally through said inner core and communicating with said pressure responsive means to receive the fluid thereof when said piston assembly means is moved through said outer sleeve and said pressure responsive means is compressed, and
   pressure indicating means for indicating the fluid pressure at which the fluid from said outer sleeve is delivered to the utilization device, said indicated fluid pressure being dependent upon the height of the fluid received in said fluid channel.

3. The manometer recited in claim 2, wherein said pressure responsive means is a flexible bellows.

4. The manometer recited in claim 2, wherein said pressure indicating means is affixed to said piston assembly means.

5. The manometer recited in claim 2, further including a hypodermic syringe and tube means connected between said outer sleeve and said syringe for delivering fluid to the utilization device by way of said tube means and syringe.

6. The manometer recited in claim 2, wherein the utilization means for receiving fluid from said manometer is a hollow occlusion cuff to be implanted in engagement with the urethra of an incontinent patient for applying occlusive pressures thereto, said pressure indicating means indicating the occlusive pressure being applied to the patient's urethra by said cuff.

7. The manometer recited in claim 6, wherein said pressure indicating means includes indicia marked on said piston assembly means and corresponding to a plurality of different circumferences of a human urethra, and means by which to initialize said indicating means such that the occlusive pressure being indicated thereby corresponds to a selected one circumference of the patient's urethra.

8. The manometer recited in claim 7, wherein said outer collar is coaxially arranged and rotatable with respect to said inner core, said outer collar having a hair line extending longitudinally therealong, and said inner core having a plurality of calibrated pressure lines traversing said hair line and corresponding to a plurality of pressures that can be applied to the patient's urethra by said occlusion cuff.

9. The manometer recited in claim 8, wherein said piston assembly means further comprises a cap located on an end of said piston assembly means opposite said pressure responsive means, said end cap having indicia marked thereon which corresponds to said plurality of urethral circumferences, said outer collar being rotatable relative to said end cap such that the hair line thereof is aligned with the selected one circumference which corresponds to the patient's urethra, the height of the fluid in said fluid channel means when said pressure responsive means is compressed corresponding to a particular pressure line at said inner core, which pressure line is indicative of the occlusive pressure being applied to the patient's urethra by said occlusion cuff.

10. The manometer recited in claim 8, further including releasable locking means by which to engage said rotatable collar and prevent the unintended rotation thereof with respect to said inner core.

11. The manometer recited in claim 10, wherein said releasable locking means includes spring means for engaging said outer collar to bias said collar towards a locked position and thereby prevent the unintended rotation thereof, said outer collar being movable against the bias of said spring means and away from the locked position to thereby permit the rotation of said outer collar with respect to said inner core.

12. The manometer recited in claim 11, wherein said releasable locking means further includes a plurality of detents formed in an end of said outer collar and pin means extending from said piston assembly means to be received by one of said detents to prevent the rotation of said collar when said spring means biases said collar into the locked position.

13. A hypodermic manometer comprising a sleeve filled with fluid to be delivered to a utilization device and a piston assembly for movement through said sleeve to force fluid outwardly therefrom, said piston assembly comprising:

resilient pressure responsive means filled with fluid and movable with said piston assembly through said fluid filled sleeve;

fluid channel means movable with said piston assembly and communicating with said pressure responsive means to receive the fluid thereof when said piston assembly is moved through said sleeve; and pressure indicating means movable with said piston assembly through said sleeve to indicate the pressure at which fluid is applied to said utilization device, the indicated pressure being dependent upon the location of the fluid in said fluid channel means when said piston assembly is moved through said sleeve;

the movement of said piston assembly through said sleeve simultaneously expulsing fluid from said sleeve for delivery to said utilization device and compressing said resilient pressure responsive means to force fluid from said responsive means into said fluid channel means to thereby provide an indication of the pressure at which the fluid from said sleeve is delivered to the utilization device.

* * * * *